(12) United States Patent
Huang et al.

(10) Patent No.: US 9,656,943 B2
(45) Date of Patent: May 23, 2017

(54) PROCESS FOR PRODUCING DIMETHYL CARBONATE

(71) Applicant: Chang Chun Plastics Co. Ltd., Taipei (TW)

(72) Inventors: Chien Fu Huang, Taipei (TW); Yi Ta Tsai, Taipei (TW)

(73) Assignee: Chang Chun Plastics Co. Ltd., Taipei (TW)

( * ) Notice: Subject to any disclaimer, the term of this patent is extended or adjusted under 35 U.S.C. 154(b) by 0 days.

(21) Appl. No.: 14/918,015

(22) Filed: Oct. 20, 2015

(65) Prior Publication Data

US 2017/0107169 A1    Apr. 20, 2017

(51) Int. Cl.
| | | |
|---|---|---|
| C07C 43/00 | (2006.01) | |
| C07C 68/06 | (2006.01) | |
| C07D 213/68 | (2006.01) | |

(52) U.S. Cl.
CPC .......... *C07C 68/065* (2013.01); *C07D 213/68* (2013.01)

(58) Field of Classification Search
None
See application file for complete search history.

(56) References Cited

U.S. PATENT DOCUMENTS

| | | |
|---|---|---|
| 2,667,497 A | 1/1954 | Cline |
| 2,993,908 A | 7/1961 | Millikan et al. |
| 3,457,282 A | 7/1969 | Polak et al. |
| 4,181,676 A | 1/1980 | Buysch et al. |
| 4,661,609 A | 4/1987 | Knifton |
| 4,691,041 A | 9/1987 | Duranleau et al. |
| 4,734,518 A | 3/1988 | Knifton |
| 4,841,072 A | 6/1989 | Harvey |
| 4,931,571 A | 6/1990 | Weinstein |
| 5,231,212 A | 7/1993 | Buysch et al. |
| 5,359,094 A | 10/1994 | Teles et al. |
| 7,605,285 B2 | 10/2009 | Kobayashi et al. |
| 8,809,569 B2 | 8/2014 | Zhang et al. |
| 9,006,498 B2 | 4/2015 | Ten Kate et al. |
| 9,051,424 B2 | 6/2015 | Lobert et al. |
| 2004/0162226 A1 | 8/2004 | Sunder et al. |
| 2005/0075258 A1 | 4/2005 | Kessler et al. |
| 2005/0113271 A1 | 5/2005 | Pegelow et al. |
| 2009/0270657 A1* | 10/2009 | Van Der Heide ..... C07C 68/065 568/852 |
| 2011/0196167 A1 | 8/2011 | Almusaiteer et al. |
| 2012/0264941 A1 | 10/2012 | Jerome et al. |
| 2013/0165669 A1 | 6/2013 | Zhao et al. |
| 2015/0152079 A1 | 6/2015 | Mignani et al. |
| 2015/0239858 A1 | 8/2015 | Lee et al. |

FOREIGN PATENT DOCUMENTS

| | | |
|---|---|---|
| CN | 1049212 C | 2/2000 |
| CN | 1074310 C | 11/2001 |
| CN | 1138736 C | 2/2004 |
| CN | 1235864 C | 1/2006 |
| CN | 1241900 C | 2/2006 |
| CN | 100364956 C | 1/2008 |
| CN | 100453540 C | 1/2009 |
| CN | 1946660 B | 11/2012 |
| WO | WO-2009016149 A2 | 2/2009 |
| WO | WO-2011157551 A1 | 12/2011 |

OTHER PUBLICATIONS

Sun et al. Xiandai Huagong (2011), 31(5), 53-55.*
Giani et al. Computers and Chemical Engineering 29 (2005) 1661-1676.*

* cited by examiner

*Primary Examiner* — Yong Chu
*Assistant Examiner* — Ana Z Muresan
(74) *Attorney, Agent, or Firm* — Polsinelli PC

(57) ABSTRACT

The present disclosure relates to a recycling method for producing dimethyl carbonate. The process is unique in that it produces a by-product that can be re-used in the process as a raw material for repeating the process. For example, when the process is directed to synthesizing dimethyl carbonate, glycerol is used as a starting material. Glycerol is also a by-product produced during formation of dimethyl carbonate, and therefore it can be re-used as starting material to generate more dimethyl carbonate.

19 Claims, 1 Drawing Sheet

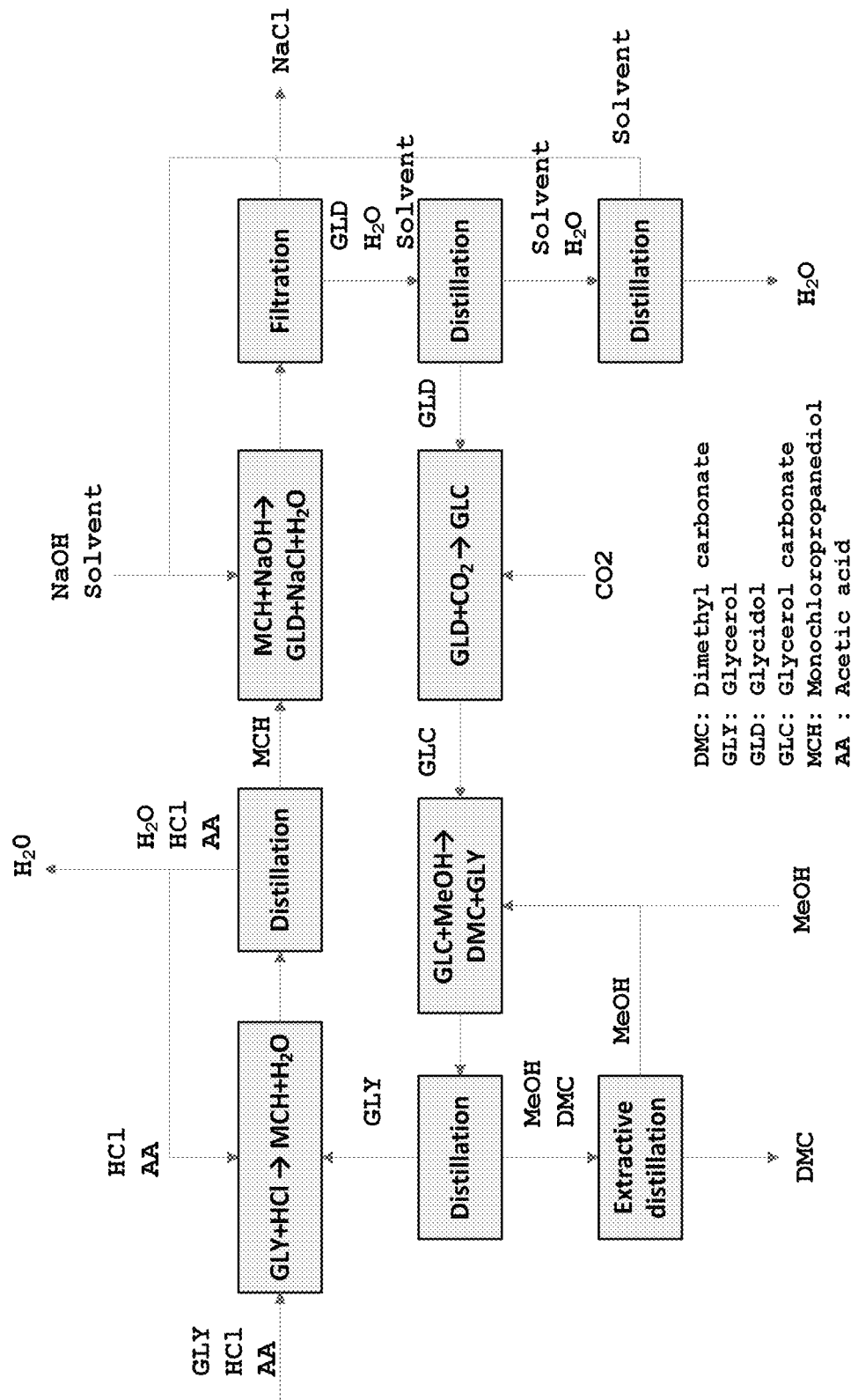

PROCESS FOR PRODUCING DIMETHYL CARBONATE

FIELD OF THE DISCLOSURE

The present disclosure relates to a method for producing dimethyl carbonate and dimethyl carbonate derivatives. The process is unique in that it produces a by-product that can be re-used in the process as a raw material for repeating the process.

BACKGROUND

Dimethyl carbonate (DMC) is an organic compound with the formula $OC(OCH_3)_2$. It is a colorless, flammable liquid. It is classified as a carbonate ester. It is useful as a methylating agent and as a solvent that is exempt from classification as a volatile organic compound (VOC) in the United States. Dimethyl carbonate is often considered to be a green reagent by minimizing the use and generation of hazardous substances. Dimethyl carbonate's main benefit over other methylating reagents such as iodomethane and dimethyl sulfate is its much lower toxicity and its biodegradability.

DMC has grown in popularity and applications as a replacement for methyl ethyl ketone, tert-butyl acetate, and parachlorobenzotrifluoride. It has an ester or alcohol like odor, which is more favorable to users than most hydrocarbon solvents it replaces. DMC has an evaporation rate of 3.22 (butyl acetate=1.0), which slightly slower than methyl ethyl ketone (MEK) (3.8) and ethyl acetate (4.1) and faster than toluene (2.0) and isopropanol (1.7). It has solubility profile similar to common glycol ethers, meaning DMC can solve most common coating resins. Hildebrand solubility parameter is 20.3 Mpa and Hansen solubility parameters are: dispersion=15.5, polar=3.9, H bonding=9.7. DMC is partially soluble in water up to 13%, however DMC has hydrolyzed in water based systems over time to methanol and $CO_2$ unless properly buffered. DMC is a flammable liquid that has a flash point of 17° C. (63° F.) making it safer than acetone, methyl acetate and methyl ethyl ketone from a flammability point of view.

SUMMARY OF THE DISCLOSURE

The present disclosure relates to a method for producing dimethyl carbonate (DMC) and dimethyl carbonate derivatives (compounds of Formula (VI)). The process is unique in that it produces a by-product that can be re-used in the process as a raw material for repeating the process. When the product of interest is dimethyl carbonate, for example, the by-product is glycerol, which can be recycled back into the process as a starting material. The process is additionally unique in that it does not produce ethylene glycol or propylene glycol as by-products. Traditional processes for producing compounds such as dimethyl carbonate involve reacting an oxirane compound with carbon dioxide, which results in the formation of ethylene glycol and propylene glycol as by-products.

In general, the instant disclosure relates to a process for producing a compound of Formula (VI) comprising:
(a) reacting a compound of Formula (I) with an halogenating agent to form a compound of Formula (II)

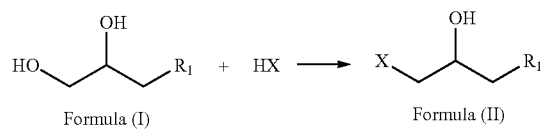

wherein, X is F, Cl, Br, or I; and $R_1$ is a hydrogen, hydroxyl, $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups;
(b) reacting the compound of Formula (II) with a base to form a compound of Formula (III)

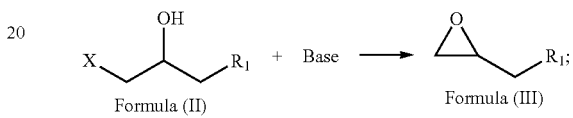

(c) reacting the compound of Formula (III) with carbon dioxide to form a compound of Formula (IV)

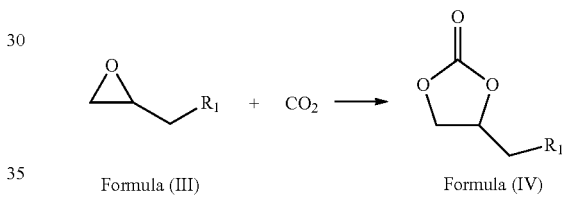

wherein, $R_1$ is a hydrogen, hydroxyl, $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups; and
(d) reacting the compound of Formula (IV) with an alcohol to form a compound of Formula (VI) and the compound of Formula (I)

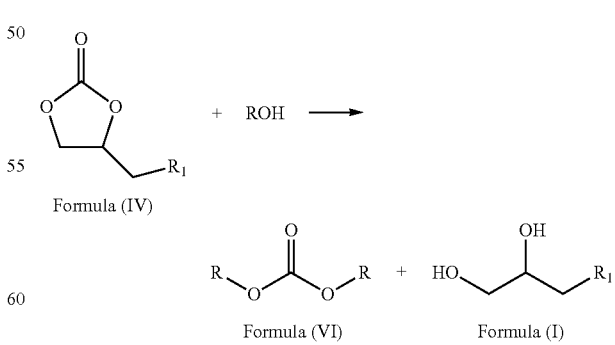

wherein, R is a $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups.

The instant disclosure also relates to a method for producing dimethyl carbonate. The method typically comprises:

(a) reacting glycerol with hydrochloric acid to form 3-chloropropane-1,2-diol and water

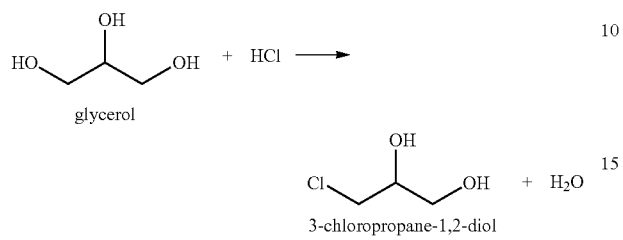

(b) reacting 3-chloropropane-1,2-diol with sodium hydroxide to form glycidol, sodium chloride, and water

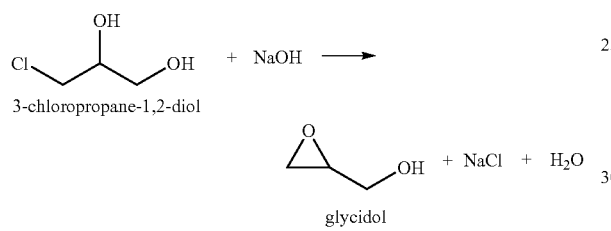

(c) reacting glycidol with carbon dioxide in the presence of potassium bromide to form glycerol carbonate

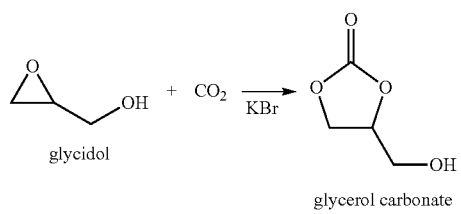

(d) reacting the glycerol carbonate with methanol in the presence of potassium hydroxide to form dimethyl carbonates and glycerol, and

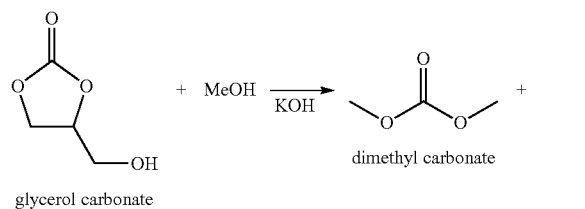

(e) recycling the glycerol formed in (d) into (a).

BRIEF DESCRIPTION OF THE DRAWINGS

Implementations of the present technology will now be described, by way of example only, with reference to the attached FIGURES, wherein:

FIG. 1 is a schematic illustrating various steps that can be included in the instant process.

It should be understood that the various aspects are not limited to the arrangements and instrumentality shown in the drawings.

DETAILED DESCRIPTION OF THE DISCLOSURE

The instant disclosure relates to a process for producing a compound of Formula (VI) comprising:

(a) reacting a compound of Formula (I) with an halogenating agent to form a compound of Formula (II)

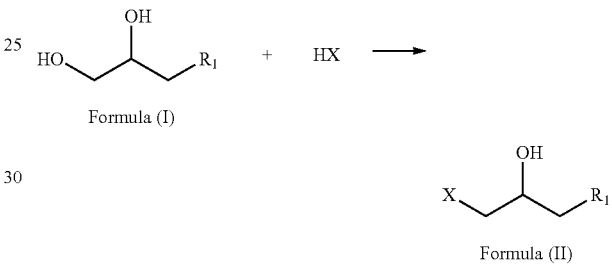

wherein, X is F, Cl, Br, or I; and $R_1$ is a hydrogen, hydroxyl, $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups;

(b) reacting the compound of Formula (II) with a base to form a compound of Formula (III)

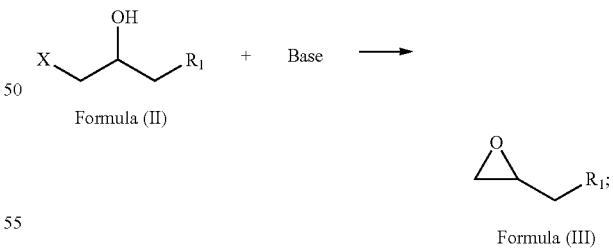

(c) reacting the compound of Formula (III) with carbon dioxide to form a compound of Formula (IV)

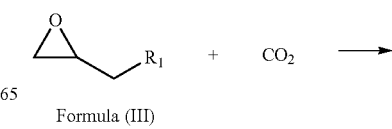

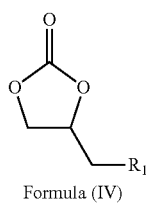

Formula (IV)

wherein, $R_1$ is a hydrogen, hydroxyl, $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups; and (d) reacting the compound of Formula (IV) with an alcohol to form a compound of Formula (VI) and the compound of Formula (I)

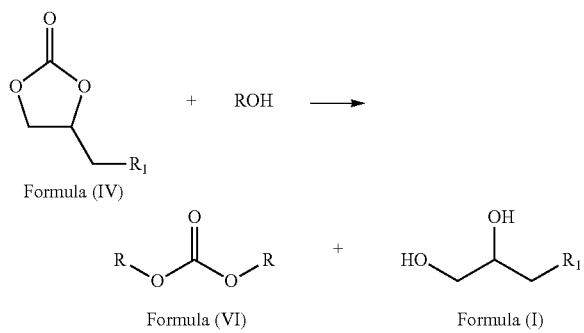

Formula (IV)    Formula (VI)    Formula (I)

wherein, R is a $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups.

The halogenating agent in (a) may be hydrogen chloride or a mixture of gaseous hydrogen chloride and an aqueous solution of hydrogen chloride. Also, the reaction of the compound of Formula (I) with the halogenating agent in (a) can be carried out in the presence of a catalyst. The catalyst may be, for example, an organic acid catalyst, and inorganic acid catalyst, or a heterogeneous acid catalyst. In some cases, the catalyst is an organic acid catalyst selected from the group consisting of a carboxylic, a sulfonic, and a phosphoric acid. In other cases, the catalyst is an organic catalyst such as acetic acid.

The base in (b) can be a hydroxide, a carbonate and a bicarbonate of alkali metal or an alkaline earth metal. In some cases, for example the base in (b) is selected from the group consisting of LiOH, NaOH, KOH, CsOH, RbOH, Mg(OH)$_2$, Ca(OH)$_2$, Sr(OH)$_2$, NH$_4$OH, Ba(OH)$_2$, K$_2$CO$_3$, NaHCO$_3$, KHCO$_3$, and basic ion exchange resin. In other cases, the base is NaOH. Furthermore, the reaction of the compound of Formula (II) with a base to form a compound of Formula (III) in (b) may be carried out in a solvent. The solvent may be, for example a $C_1$-$C_6$ alcohol. In some cases, the solvent is isopropyl alcohol or methanol.

Examples of basic ion exchange resins are provided in the table below.

| Grade name | Chemical structure or Functional group |
|---|---|
| DIAION PA312 | —CH$_2$—CH— (phenyl with CH$_2$N$^+$(CH$_3$)$_3$ Cl$^-$) |
| DIAION PA316 | —CH$_2$—CH— (phenyl with CH$_3$, CH$_2$N$^+$(CH$_3$)$_2$ Cl$^-$) |
| AMBERLITE UP900 | Trimethyl ammonium |
| Purolite A500Plus | Type I Quaternary Ammonium |
| DIAION WA20 | —CH$_2$—CH— (phenyl with CH$_2$NH(CH$_2$CH$_2$NH)$n$H) |

The reaction of the compound of Formula (III) with carbon dioxide in (c) is often carried out in the presence of a catalyst, such as an alkali metal halide salt. Alkali metal halide salts include, for example, NaCl, NaBr, NaI, KCl, KBr and KI.

The reaction of the compound of Formula (IV) with alcohol in (d) is also often carried out in the presence of a catalyst. Useful catalysts include, for example, a hydroxide, carbonates and bicarbonates of alkali metals and alkaline earth metals. In some cases, the catalyst is a base selected from the group consisting of LiOH, NaOH, KOH, CsOH, RbOH, Mg(OH)$_2$, Ca(OH)$_2$, Sr(OH)$_2$, NH$_4$OH, Ba(OH)$_2$, Na$_2$CO$_3$, NaHCO$_3$, K$_2$CO$_3$ and KHCO$_3$. In other cases, the base is KOH.

The instant disclosure also relates specifically to a process for producing dimethyl carbonate, the process comprising:

(a) reacting glycerol with a hydrogen halide to form a compound of Formula (II-a);

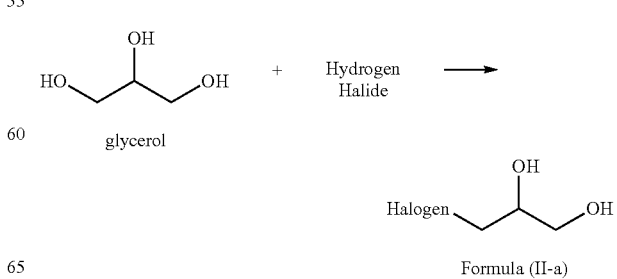

glycerol

Formula (II-a)

(b) reacting the compound of Formula (II-a) with a base to form glycidol,

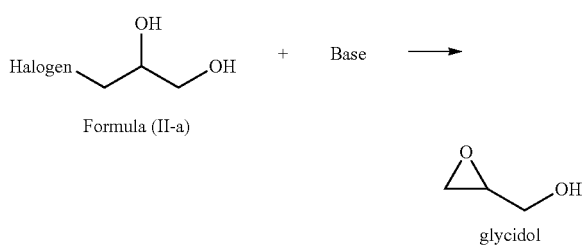

Formula (II-a)

glycidol (c) reacting the glycidol with carbon dioxide to form glycerol carbonate; and

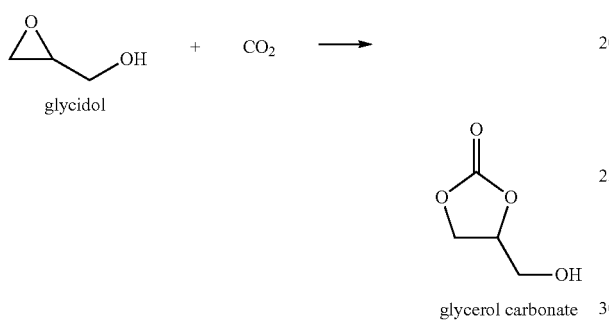

glycidol glycerol carbonate (d) reacting the glycerol carbonate with methanol to form dimethyl carbonate and glycerol

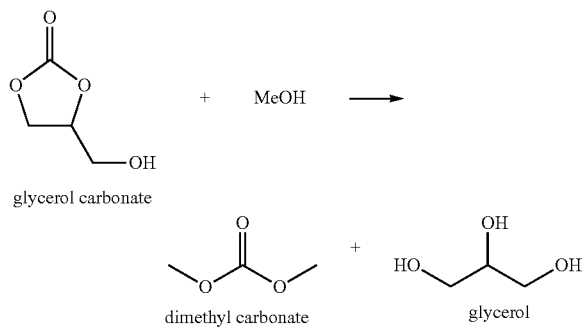

glycerol carbonate dimethyl carbonate glycerol

The hydrogen halide in (a) may be, for example, HCl and the compound of Formula (II-a) may be, for example, 3-chloropropane-1,2-diol. Furthermore, the reaction of glycerol with the hydrogen halide in (a) may be carried out in the presence of a catalyst. The catalyst may be an organic acid catalyst, an inorganic acid catalyst, or a heterogeneous acid catalyst. In some cases, the catalyst is an organic acid catalyst selected from the group consisting of a carboxylic, a sulfonic, and a phosphoric acid. In other cases, the organic acid catalyst is acetic acid.

The base in (b) may be, for example, a hydroxide, a carbonate and a bicarbonate of alkali metal and alkaline earth metal. In some cases, the base in (b) is selected from the group consisting of LiOH, NaOH, KOH, CsOH, RbOH, Mg(OH)$_2$, Ca(OH)$_2$, Sr(OH)$_2$, NH4OH, Ba(OH)2, Na$_2$CO$_3$, and K$_2$CO$_3$, NaHCO$_3$ KHCO$_3$, and a basic ion exchange resin. In other cases, the base is NaOH. The reaction of the compound of Formula (II) with a base to form a compound of Formula (III) in (b) can be carried out in a solvent, such as a solvent selected from the group consisting of $C_1$-$C_6$ alcohol. In some cases, the solvent is isopropyl alcohol or methanol.

The reaction of glycidol with carbon dioxide in (c) can be carried out in the presence of a catalyst. For example, the catalyst may be an alkali metal halide salt. Examples of alkali metal halide salts include, but are not limited to, NaCl, NaBr, NaI, KCl, KBr and KI.

The reaction of the compound of Formula (IV) with methanol in (d) can be carried out in the presence of a catalyst. The catalyst may be, for example, a hydroxide, a carbonate or a bicarbonate of alkali metal, or an alkaline earth metal. In some cases, the catalyst is a base selected from the group consisting of LiOH, NaOH, KOH, CsOH, RbOH, Mg(OH)$_2$, Ca(OH)$_2$, Sr(OH)$_2$, NH$_4$OH, Ba(OH)$_2$, Na$_2$CO$_3$, NaHCO$_3$, K$_2$CO$_3$ and KHCO$_3$. In other cases, the base is KOH.

The instant disclosure further relates to a method for producing dimethyl carbonate comprising:

(a) reacting glycerol with hydrochloric acid to form 3-chloropropane-1,2-diol and water

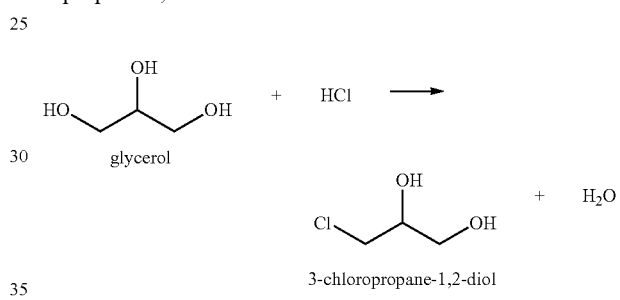

glycerol 3-chloropropane-1,2-diol (b) reacting 3-chloropropane-1,2-diol with sodium hydroxide to form glycidol, sodium chloride, and water

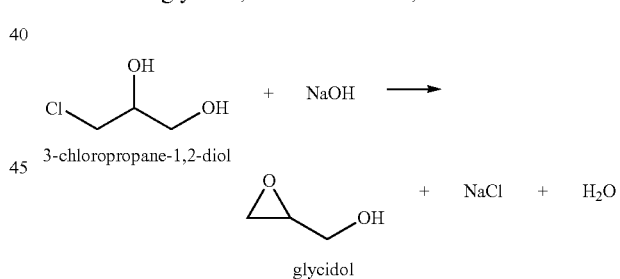

3-chloropropane-1,2-diol glycidol (c) reacting glycidol with carbon dioxide in the presence of potassium bromide to form glycerol carbonate

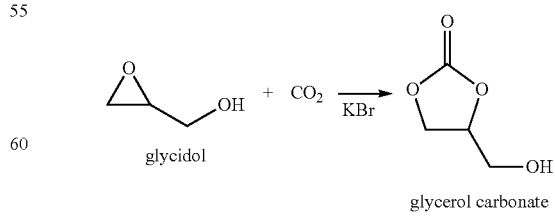

glycidol glycerol carbonate (d) reacting the glycerol carbonate with methanol in the presence of potassium hydroxide to form dimethyl carbonates and glycerol, and

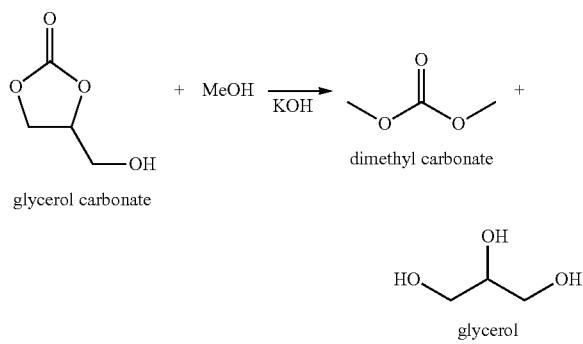

(e) recycling the glycerol formed in (d) into (a).

In some cases the reaction of the glycerol with hydrochloric acid in (a) is carried out in the presence of a catalyst, such as, for example, an organic acid catalyst selected from the group consisting of carboxylic, sulfonic, and phosphoric acids. In other cases, the organic acid catalyst is acetic acid. Finally, the water produced in (a) and/or (b) can be removed by distillation; and the sodium chloride produced in (b) can be removed by filtration.

Example 1

Synthesis of Dimethyl Carbonate

A Glycerol(224.76 g), acetic acid(14.47 g), and 37%-hydrogen chloride solution (360.29 g) was placed in a 1 liter glass reactor, and then stirred using an agitator. The solution was heating to 100° C. for 2 hours at 1 atm pressure. The product was analysed by GC, and the conversion of glycerol was 51.91%, and the selectivity of 3-chloropropane-1,2-diol was 79.37%.

3-chloropropane-1,2-diol (112.9 g), 49.5% NaOH (80.8 g), and isopropanol (320.1 g) were placed in a 1 liter glass reactor, and stirred with an agitator. The solution was heating to 30° C. for 2 hours at 1 atm pressure. The product was analysed by GC, and the conversion of 3-chloropropane-1,2-diol was 88.6%, and the selectivity of glycidol was 96%.

Potassium bromide was used to catalyze the reaction of glycidol to glycerol carbonate using carbon dioxide. In a 150 mL stainless steel autoclave, enough potassium bromide was added to equal 500 ppm (0.02 g) of the glycidol charged (0.54 moles=40 g of glycidol). Glycidol and potassium bromide was charged to the 150 mL stainless steel autoclave, and then the autoclave was filled with carbon dioxide. At room temperature the carbon dioxide was added to bring the initial pressure to 29.4 bar and the reaction was begun by heating to 100° C. Carbon dioxide was continually added to the autoclave to maintain this pressure. After a 10.5 hour reaction period, the reactor was cooled and vented, and the product was recovered. The results are presented in the table below (Inventive Example 1) and contrasted with a comparative example from U.S. Pat. No. 4,931,571, which describes the formation of ethylene carbonate from ethylene oxide.

| | Charge | Temp (° C.) | Pressure (bar) | Time (hour) | Conversion (%) | Selectivity (%) |
|---|---|---|---|---|---|---|
| Inventive Example 1 | 0.54 mol (glycidol) | 100 | 29.4 | 10.5 | 100 (glycidol) | 90.2 (glycerol carbonate) |
| Comparative Example U.S. Pat. No. 4,931,571 | 2.22 mol (ethylene oxide) | 150 | 42.4 | 2 | 84.8 (ethylene oxide) | 91.4 (ethylene carbonate) |

Glycerol carbonate (19.14 g), methanol (21.70 g), and potassium hydroxide (0.22 g) were placed in a 150 mL stainless steel autoclave, and then the autoclave was filled with nitrogen to 10 kg/cm² at room temperature. The reaction was begun by heating to 100° C., and this temperature was maintained for 3 hours. The reaction pressure was 15 kg/cm² (increased with temperature, 30° C.→100° C., 10 kg/cm²→15 kg/cm²). The product was analyzed by GC. The conversion of glycerol carbonate was 47.02%, and the selectivity of dimethyl carbonate was 81%, and the selectivity of glycerol was 75%.

Example 2

Synthesis of Diethyl Carbonate

Diethyl carbonate may be prepared by using 0.2 g potassium hydroxide catalyst dissolved in 20.08 g (0.17 mole) of glycerol carbonate. 78.32 g (1.7 mole) ethanol is added to the mixture. The mixture is placed in a 150 mL stainless steel autoclave, and then filled with nitrogen to 10 kg/cm² at room temperature and the reaction is begun by heating to 100° C. The reaction temperature is maintained at about 100° C. for 3 hours, and reaction pressure is 15 kg/cm² (increased with temperature, 30° C.→100° C., 10 kg/cm²→15 kg/cm²).

Example 3

Synthesis of Diisopropyl Carbonate

Diisopropyl carbonate may be prepared by using 0.2 g potassium hydroxide catalyst dissolved in 20.08 g (0.17 mole) of glycerol carbonate. 102.17 g (1.7 mole) isopropanol is added to the mixture. The mixture is placed in a 150 mL stainless steel autoclave, and then the autoclave is filled with nitrogen to 10 kg/cm² at room temperature and the reaction is begun by heating to 100° C. The reaction temperature is maintained at about 100° C. for 3 hours, and reaction pressure is 15 kg/cm² (increased with temperature, 30° C.→100° C., 10 kg/cm²→15 kg/cm²).

Example 4

Synthesis of Diphenyl Carbonate

Diphenyl carbonate may be prepared by using 0.2 g potassium hydroxide catalyst dissolved in 20.08 g (0.17 mole) of glycerol carbonate. 159.99 g (1.7 mole) phenol is added to the mixture. The mixture is placed in a 150 mL stainless steel autoclave, and the autoclave is filled with nitrogen to 10 kg/cm² at room temperature and the reaction is begun by heating to 100° C. The reaction temperature is maintained at about 100° C. for 3 hours, and reaction pressure is 15 kg/cm² (increased with temperature, 30° C.→100° C., 10 kg/cm²→15 kg/cm²).

Example 5

Synthesis of Di(piperidin-4-yl) Carbonate

Di(piperidin-4-yl) Carbonate may be prepared by using 0.2 g potassium hydroxide catalyst dissolved in 20.08 g (0.17 mole) of glycerol carbonate. 171.96 g (1.7 mole) 4-piperidinol is added to the mixture. The mixture is placed in a 150 mL stainless steel autoclave, and the autoclave is filled with nitrogen to 10 kg/cm$^2$ at room temperature and the reaction is begun by heating to 100° C. The reaction temperature is maintained at about 100° C. for 3 hours, and reaction pressure is 15 kg/cm$^2$ (increased with temperature, 30° C.→100° C., 10 kg/cm$^2$→15 kg/cm$^2$).

The above embodiments are only used to illustrate the principle of the present disclosure and the effect thereof, and should not be construed as to limit the present disclosure. The above embodiments can be modified and altered by those skilled in the art, without departing from the spirit and scope of the present disclosure. Therefore, the protection scope of the present disclosure is defined in the following appended claims. As long as it does not affect the effects and achievable goals of this disclosure, it should be covered under the technical contents disclosed herein.

The terms "comprising," "having," and "including" are used in their open, non-limiting sense. The terms "a" and "the" are understood to encompass the plural as well as the singular. The expression "at least one" means one or more and thus includes individual components as well as mixtures/combinations. The term "about" when referring to a value, is meant specifically that a measurement can be rounded to the value using a standard convention for rounding numbers. For example, "about 1.5" is 1.45 to 1.54. All valued set forth herein can be modified with the term "about" or recited without the term, regardless of whether the term "about" is specifically set forth (or is absent) in conjunction with any particular value. All ranges and values disclosed herein are inclusive and combinable. For examples, any value or point described herein that falls within a range described herein can serve as a minimum or maximum value to derive a sub-range, etc.

The invention claimed is:

1. A process for producing a compound of formula (VI) comprising:
    (a) reacting a compound of formula (I)

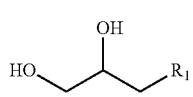

formula (I)

with a halogenating agent to form a compound of formula (II)

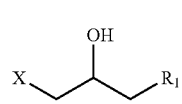

formula (II)

wherein, the halogenating agent is represented by HX, wherein X is F, Cl, Br, or I; and R$_1$ is selected from the group consisting of, hydroxyl, C$_1$-C$_8$ alkyl, C$_1$-C$_8$ alkenyl, C$_1$-C$_8$ alkoxy, C$_3$-C$_8$ cycloalkyl, C$_6$-C$_{10}$ aryl group and a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups;

(b) reacting the compound of formula (II) with a base in a solvent selected from the group consisting of C$_1$-C$_6$ alcohol to form a compound of formula (III)

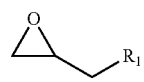

formula (III)

(c) reacting the compound of formula (III) with carbon dioxide to form a compound of formula (IV)

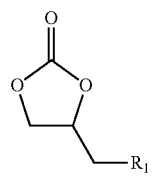

formula (IV)

(d) reacting the compound of formula (IV) with an alcohol to form a compound of formula (VI) and the compound of formula (I)

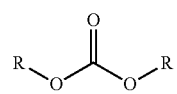

(formula (VI))

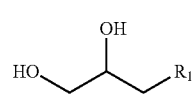

formula (I)

wherein,
    the alcohol is represented by ROH, wherein R is selected from the group consisting of a C$_1$-C$_8$ alkyl, C$_1$-C$_8$ alkenyl, C$_1$-C$_8$ alkoxy, C$_3$-C$_8$ cycloalkyl, C$_6$-C$_{10}$ aryl group and a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups; and (e) recycling the compound of formula (I) formed in (d) into (a) and repeating the chemical reactions of (a)-(d) using the compound of formula (I) formed in (d) as starting material.

2. The process of claim 1, wherein the halogenating agent in (a) is hydrogen chloride or a mixture of gaseous hydrogen chloride and an aqueous solution of hydrogen chloride.

3. The process of claim 1, wherein the reaction of the compound of formula (I) with an acid in (a) is carried out in the presence of a catalyst.

4. The process of claim 3, wherein the catalyst is an organic acid catalyst, an inorganic acid catalyst, or a heterogeneous acid catalyst.

5. The process of claim 4, wherein the catalyst is an organic acid catalyst selected from the group consisting of a carboxylic, a sulfonic, and a phosphoric acid.

6. The process of claim 1, wherein the base in (b) is selected from the group consisting of a hydroxide, a carbonate and a bicarbonate of alkali metal, alkaline earth metal, and a basic ion exchange resin.

7. The process of claim 6, wherein the base in (b) is selected from the group consisting of LiOH, NaOH, KOH, CsOH, RbOH, $Mg(OH)_2$, $Ca(OH)_2$, $Sr(OH)_2$, $NH_4OH$, $Ba(OH)_2$, $Na_2CO_3$, and $K_2CO_3$, $NaHCO_3$ and $KHCO_3$.

8. The process of claim 1, wherein the reaction of the compound of formula (III) with carbon dioxide in (c) is carried out in the presence of a catalyst.

9. The process of claim 8, wherein the catalyst is an alkali metal halide salt.

10. The process of claim 9, wherein the alkali metal halide salt is selected from NaCl, NaBr, NaI, KCl, KBr and KI.

11. The process of claim 1, wherein the reaction of the compound of formula (IV) with alcohol in (d) is carried out in the presence of a catalyst.

12. The process of claim 11, wherein the catalyst is selected from the group consisting of a hydroxide, and a carbonate and a bicarbonate of alkali metal and alkaline earth metal.

13. The process of claim 12, wherein the catalyst is a base selected from the group consisting of LiOH, NaOH, KOH, CsOH, RbOH, $Mg(OH)_2$, $Ca(OH)_2$, $Sr(OH)_2$, $NH_4OH$, $Ba(OH)_2$, $Na_2CO_3$, $NaHCO_3$, $K_2CO_3$ and $KHCO_3$.

14. The process of claim 13, wherein the base is KOH.

15. The process of claim 1, wherein the alcohol in (d) is methanol.

16. A process for producing dimethyl carbonate comprising:
(a) reacting glycerol with hydrochloric acid to form 3-chloropropane-1,2-diol and water,
(b) reacting 3-chloropropane-1,2-diol with sodium hydroxide in a solvent selected from the group consisting of $C_1$-$C_6$ alcohol to form glycidol, sodium chloride, and water,
(c) reacting glycidol with carbon dioxide in the presence of potassium bromide to form glycerol carbonate,
(d) reacting the glycerol carbonate with methanol in the presence of potassium hydroxide to form dimethyl carbonates and glycerol, and
(e) recycling the glycerol formed in (d) into (a) and repeating the chemical reactions of (a)-(d) using the glycerol formed in (d) as starting material.

17. The process of claim 16, wherein the reaction of the glycerol with hydrochloric acid in (a) is carried out in the presence of a catalyst.

18. The process of claim 17, wherein the catalyst is an organic acid catalyst selected from the group consisting of carboxylic, sulfonic, and phosphoric acids.

19. The process of claim 18, wherein the organic acid catalyst is acetic acid.

* * * * *